United States Patent [19]

Sfikas

[11] Patent Number: 5,695,477
[45] Date of Patent: Dec. 9, 1997

[54] NEEDLE EJECTOR SAFETY SYSTEM

[76] Inventor: John Sfikas, 2834 W. Rascher, Chicago, Ill. 60625

[21] Appl. No.: 331,077

[22] Filed: Oct. 28, 1994

[51] Int. Cl.$^6$ ................................................. A61M 5/00
[52] U.S. Cl. .................. 604/241; 604/239; 604/187; 128/919
[58] Field of Search .................. 128/919; 604/187, 604/200, 201, 239, 230, 241, 243, 110, 192, 195, 194

[56] References Cited

U.S. PATENT DOCUMENTS

| | | | |
|---|---|---|---|
| 4,822,343 | 4/1989 | Beiser | 604/187 |
| 4,904,244 | 2/1990 | Harsh et al. | 604/187 |
| 5,088,985 | 2/1992 | Deras | 604/192 |
| 5,201,716 | 4/1993 | Richard | 604/187 |
| 5,245,935 | 9/1993 | Fukuda | 128/919 |
| 5,282,428 | 2/1994 | Grenville et al. | 128/919 |

*Primary Examiner*—Corrine M. McDermott
*Assistant Examiner*—Cris L. Rodriguez
*Attorney, Agent, or Firm*—Michael R. McKenna

[57] ABSTRACT

A safety needle system for use with a hollow syringe-like body which uses a needle for aspirating, injecting or collecting having a reciprocal guide for linearly guiding the needle into and out of operable engagement with the syringe-like body. The needle safety system permits the controlled release of a used needle so that it can be placed safely in a receptacle without danger of it going elsewhere. The structure also permits the reuse of the hollow syringe-like body. The needle safety system can be retrofitted onto existing syringe-like bodies or incorporated into syringe-like bodies during manufacture.

18 Claims, 2 Drawing Sheets

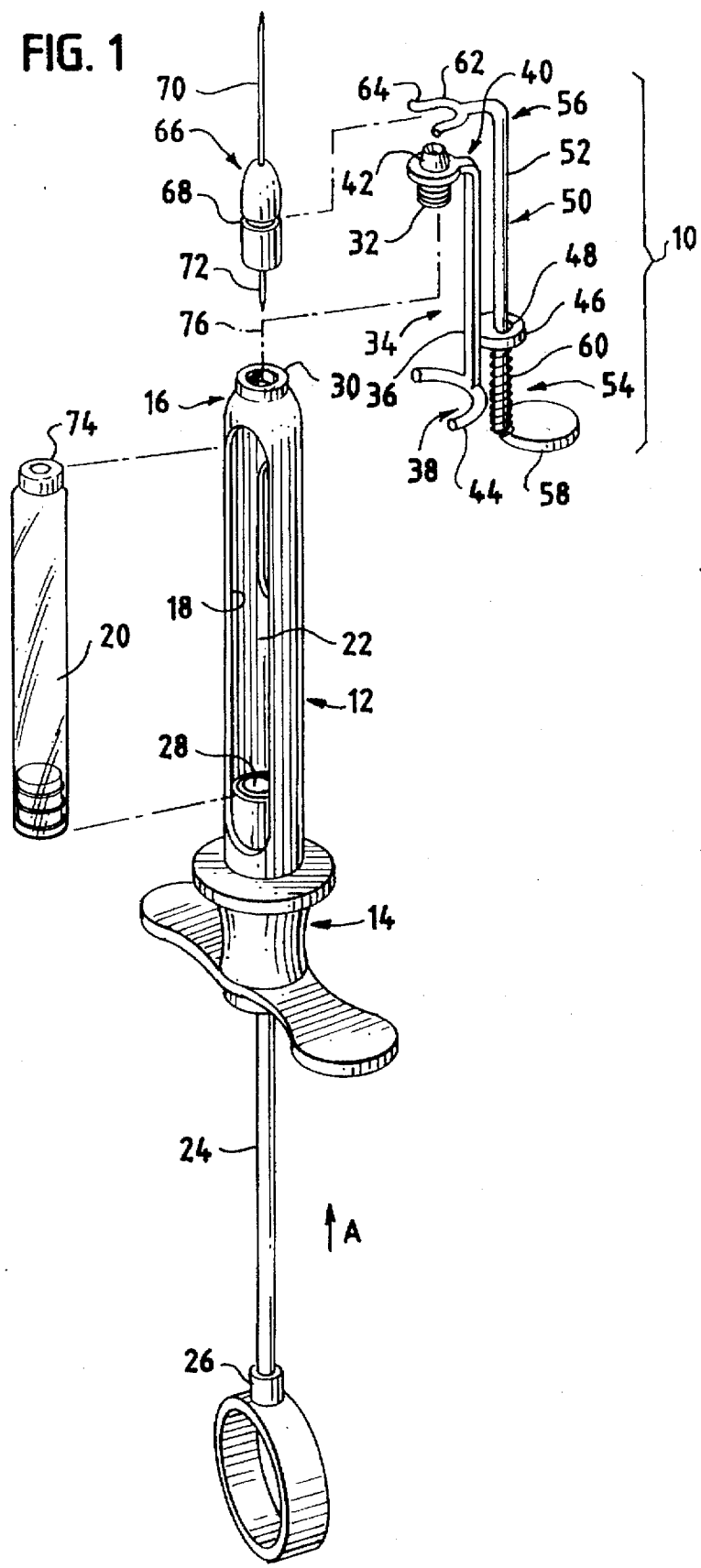
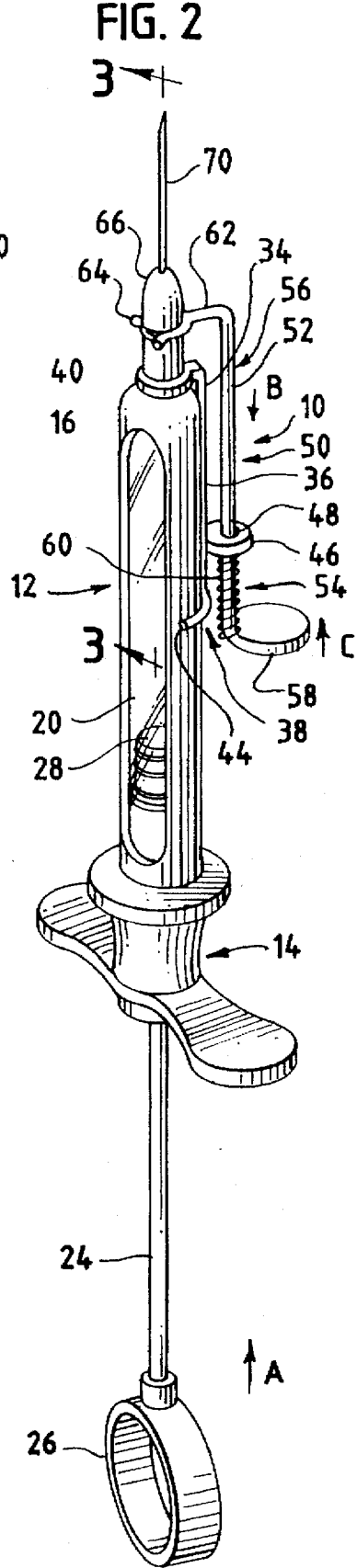

NEEDLE EJECTOR SAFETY SYSTEM

TECHNICAL FIELD

This invention generally relates to safety devices for needles used in the medical field. More particularly, the invention relates to a needle safety system to inhibit accidental contact with the needle.

BACKGROUND OF THE INVENTION

Various types of medical needles currently exist that cooperate with a hollow syringe-like body for aspirating, injecting or collecting body fluids, tissue, medicants or the like. The needles must be very sharp to quickly and easily puncture the patient's skin.

The needles often come with protective caps that eliminate the chance of accidental contact, especially of an accidental puncture. During removal of the cap, it is unlikely that an accidental contact will occur. However, misjudgment of the location of the needle when replacing the needle cap after use often times results in the needle cap not being placed over the needle and accidental contact, usually in the form of a puncture, occurring even through protective gloves. This is due in part to the needle being thin and hard to see, especially in low light conditions. Serious consequences can arise since the used needle has been exposed to the skin or blood or other body fluids of a patient, along with the viruses or bacteria that the patient may have. The needle can transfer the skin or fluids, and hence the viruses or bacteria, from the patient.

Various types of diseases are known to be conveyed by such an accident, including hepatitis and cholera.

An even more menacing and lethal virus, the Acquired Immunity Deficiency Syndrome (AIDS) virus is easily communicated by an accidental puncture. Since there is no know cure for AIDS at this time, the result of an accidental puncture can be deadly.

Many types of devices have been developed in an effort to address this problem.

Representative devices include those disclosed in U.S. Pat. Nos. 4,822,343 to Beiser and 5,201,716 to Richard. Both of these devices have pivotally mounted arms whose arcuate movement forcefully ejects the needle after use. These devices do not hold the needle as it is being removed. Ejection provides little control over where the needle goes and can result of loss of the needle or accidental contact with the needle.

Numerous other devices, such as those disclosed in U.S. Pat. No. 5,122,118 to Haber, U.S. Pat. No. 5,211,628 to Marshall, and U.S. Pat. No. 5,211,629 to Pressley et al., draw the needle into the hollow syringe-like body after use to prevent accidental contact with the needle. Unfortunately, these devices render the syringe-like body unusable and therefore are undesirable.

Many of these safety devices cannot be retrofitted onto existing hollow syringe-like bodies. Thus, these devices cannot be used on existing syringe-like bodies which leaves a health care provider with the unpleasant choice between disposing of these otherwise perfectly good instruments or risking accidental contact with the resulting consequences.

A needle safety system that permits the controlled release of a used needle and the reuse of the hollow syringe-like body and that can be retrofitted onto existing syringe-like bodies or incorporated into syringe-like bodies during manufacture is highly desirable.

SUMMARY OF THE INVENTION

The invention provides a medical needle safety system for use with a hollow syringe-like body for aspirating, injecting or collecting and a needle. The needle safety system includes a reciprocal guide for guiding the needle linearly out of operable engagement with the syringe-like body. The reciprocal guide is arranged and adapted to be positioned adjacent to the syringe-like body and includes a needle holder.

When the needle safety system is to be retrofitted on an existing syringe-like body, the needle safety system includes a protrusion for attaching the needle safety system to the syringe-like body. The reciprocal guide also includes a support arm that extends from the protrusion and which has a mount that slidably receives the reciprocal guide.

The structure permits the reciprocal guide to be extended linearly away from a distal end of the syringe-like body by pushing thereon with a finger. When the finger is removed, a spring urges the needle toward operable engagement with the syringe-like body to permit aspiration, injection or collection through the needle.

To dispose of the used contaminated needle, the syringe-like body is positioned horizontally over an appropriate bio-contaminate waste receptacle for the needle. The reciprocal guide is extended to disengage the needle from the syringe-like body. The syringe-like body is positioned to point the needle holder downward to quickly release the needle without requiring human contact with the needle. If needed, the syringe-like body can be gently tapped on the receptacle to release the needle while still not requiring human contact with the needle. In general, the needle can be disposed of safely with one hand. The syringe-like body and needle safety system can then be reused. The structure permits the controlled release of the needle so that the needle can be placed safely in the receptacle without danger of it going elsewhere.

Numerous other advantages and features of the present invention will become readily apparent from the following detailed description of the preferred embodiments and the appended claims.

BRIEF DESCRIPTION OF THE DRAWING

FIG. 1 is an exploded perspective view of a preferred embodiment of a needle safety system and a representative syringe-like body and needle housing with which it can be used.

FIG. 2 is a perspective view of the preferred embodiment of the needle safety system engaged to the syringe-like body and a needle.

DETAILED DESCRIPTION OF THE PREFERRED EMBODIMENTS

Figure 3:
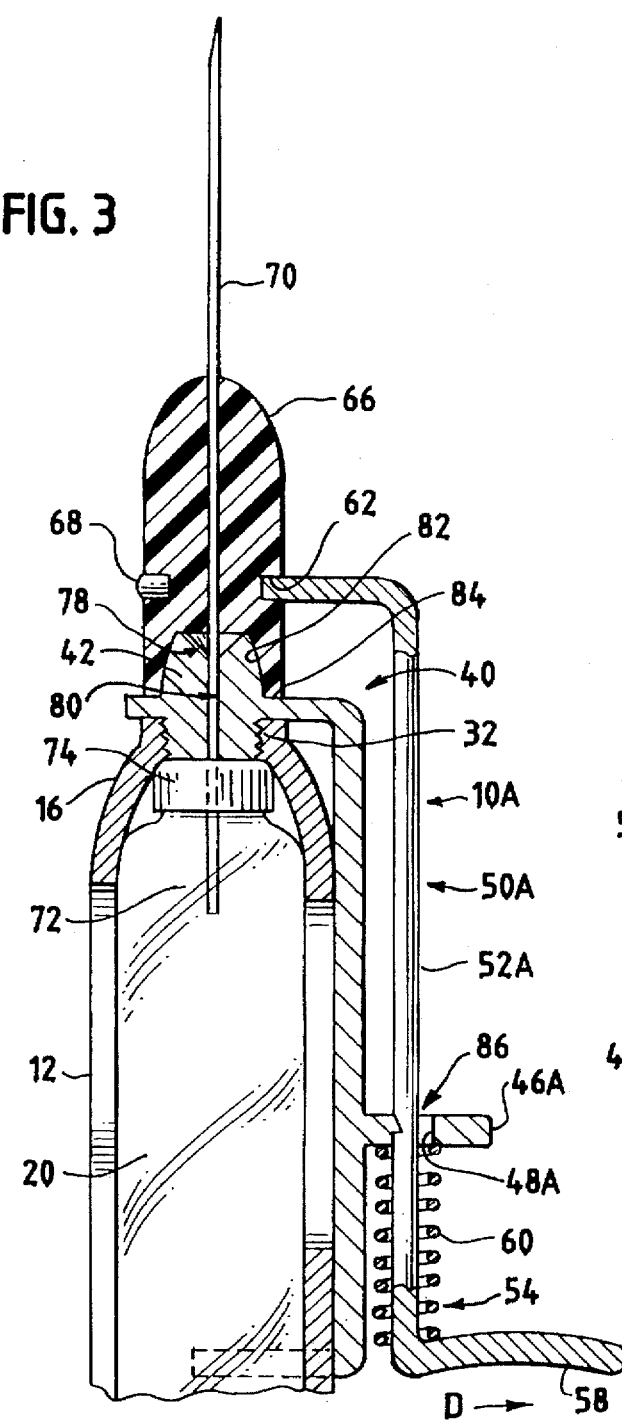
FIG. 3 is an enlarged fragmentary cross-sectional view of the preferred embodiment of the needle safety system attached to the syringe-like body.

Although this invention is susceptible to embodiment in many different forms, there are described in detail and illustrated in the drawing herein preferred embodiments of the invention. It should be understood, however, that the present disclosure is to be considered as an exemplification of the principles of this invention and is not intended to limit the invention to the embodiments described.

The needle safety system disclosed herein is suitable for use with any hollow syringe-like body for aspirating, injecting or collecting body fluids, tissue, medicants or the like, that uses a needle. Representative hollow syringe-like bodies include blood collection tubes and syringes. The needle safety system is described herein as being used with a dental syringe, although it can be used with other hollow syringe-like bodies.

FIGS. 1 and 2 illustrate a needle safety device 10 for use with a hollow syringe-like body 12 illustrated as a dental syringe body. Between proximate and distal ends 14, 16, respectively, of the syringe-like body 12 is an opening 18 through which a vial 20 containing medicant can be inserted into a cavity 22. When assembled (FIG. 2), rod 24 is moved in the direction indicated by arrow A by applying force to a ring 26 at one end of the rod 24. This movement drives a plunger 28 at the other end of the rod 24 into the vial 20 to force the medicant out of the vial 20.

A bore 30 through the syringe-like body 12 at the syringe-like body distal end 16 receives protrusion 32 to attach the needle safety device 10 to the syringe-like body 12. Guide support 34 includes a support arm 36 having proximate and distal ends 38, 40, respectively. The support arm distal end 40 includes a 90° bend and includes the protrusion 32. After the needle safety device 10 is attached to the syringe-like body 12, the support arm 36, other than the support arm distal end 40, is adjacent and parallel to the syringe-like body 12. A needle guide 42 extends from the support arm distal end 40 in a direction opposite that of the protrusion 32. An optional saddle 44 located at the support arm proximate end 38 helps support the needle safety device 10 and contributes to its stability.

Extending substantially perpendicular from the support arm 36 is a mount 46 having a hole 48 that slidably receives a reciprocal guide 50. Engagement arm 52 of the reciprocal guide 50 has proximate and distal ends 54, 56, respectively. Pad 58 extends substantially perpendicular from the engagement arm proximate end 54. Compression spring 60 has a section of the engagement arm 52 passing therethrough and is positioned between the mount 46 and the pad 58 to urge the engagement arm distal end 56 towards the syringe-like distal end 16 when the needle safety system 10 is attached thereto. The engagement arm distal end 56 has a 90° bend to parallel the support arm distal end 40 and it extends in a direction opposite that of the pad 58. The engagement arm distal end 56 terminates in a needle housing holder 62 which is generally C-shaped. Fingers 64 extend outwardly from the needle housing holder 62 in opposite directions to facilitate insertion of a needle housing 66. Groove 68 extends around the perimeter of the needle housing 66 and is received by the needle housing holder 62. Needle 70 extends through the needle housing 66 in a direction substantially perpendicular to the needle housing holder 62 and terminates in a needle stem 72. When in operable association, the needle stem 72 pierces the cap 74 of the vial 20 to permit access to the medicant in the vial 20.

In use, the vial 20 is inserted into the cavity 22 of the syringe-like body 12 having the needle safety device 10 attached thereto. At this stage, the needle housing 66 has yet to be positioned in the needle housing holder 62. A force is applied to the pad 58, typically with the user's thumb, in the direction indicated by arrow C (FIG. 2) to compress the spring 60 and urge the needle housing holder 62 away from the needle guide 42 a distance sufficient to permit the needle housing 66 to be inserted into the needle housing holder 62. To facilitate insertion of the needle housing 68, the syringe-like body 12 is preferably held parallel to the ground. The groove 68 receives the holder 62. Then, the force is removed from the pad 58, permitting the spring 60 to urge the engagement arm distal end 56 towards the needle guide 42 linearly along a central axis 76 of the syringe-like body 12 in the direction indicated by arrow B. The needle guide 42 receives the needle stem 72 and aligns the needle stem 72 so that it passes through the needle guide 42 and the protrusion 32 into the syringe-like body 12. The needle stem 72 then pierces the cap 74 and the medicant in the vial 20 can then be injected.

After the medicant of the vial 20 is injected and the needle 70 has been used, the needle 70 can be quickly released to minimize the time that the used needle 70 is exposed for accidental contact. The syringe-like body 12 is held horizontally over a bio-contaminant waste receptacle (not shown) with the needle housing holder 62 facing upward. A force is applied to the pad 58 to again compress the spring 60 and linearly move the used needle 70 out of operable engagement with the syringe-like body 12. The force urges the engagement arm distal end 56 away from the needle guide 42 to pull the needle stem 72 from the cap 74, back through the syringe-like body 12, protrusion 32 and needle guide 42. The syringe-like body 12 can then be rotated 180° so that the needle housing holder 62 is pointing downward to permit the needle housing holder 62, and hence the used needle 70, to drop into the receptacle. If needed, the syringe-like body 12 may be gently tapped to help displace the needle housing 66. The control of the release of the needle 70 achieved by the structure permits accurate placement of the needle 70 which lessens the likelihood of the needle 70 being misplaced or accidently contacted.

FIG. 3 illustrates an enlarged fragmented sectional view of the syringe-like body distal end 16 having the needle safety device 10A attached thereto. The needle stem 72 has pierced the cap 74 and terminates in the vial 20. The needle guide 42 has a frusto-conical opening 78 that helps guide the needle stem 72 into the passage 80 through the needle guide 42 and the protrusion 32.

The groove 68 receives the needle housing holder 62. The needle housing 66 has a recess 82 that receives the needle guide 42. Shoulder 84 of the needle housing 66 rests on the support arm distal end 40. Preferably, the spring 60 is still under a slight compression when the shoulder 84 contacts the support arm distal end 40 to continually urge the shoulder 84 into contact with the support arm distal end 40. Alternatively, when the mount is integral with the syringe-like body, the shoulder is continually urged into contact with the syringe-like body distal end. This alternative is not illustrated. The needle housing holder 62 inhibits linear movement of the needle housing 66, and hence linear movement of the needle 70, relative to the syringe-like body 12. The cooperation of the needle guide 42 with the recess 82 provides improved stability, especially lateral stability. The interaction of the shoulder 84 with the support arm distal end 40 also enhances stability, especially linear stability. The stability is further improved by the spring 60 still being under a compressive force when the needle housing 66 is in position. The improved stability provided individually and collectively by these structures facilitates insertion and removal of the needle into and out of a patient.

Figure 4:
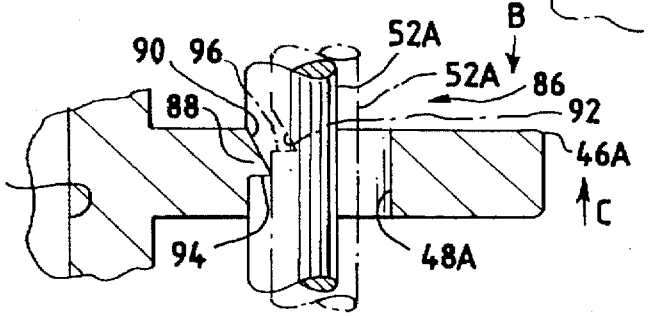
FIG. 4 is an enlarged fragmentary view of a preferred embodiment of a locking mechanism for the needle safety device.

As can be seen in FIGS. 3 and 4, the needle safety device 10A can include a locking mechanism 86 to prevent accidental movement of the pad 58, and hence the reciprocal guide 50A, in the direction indicated by arrow C to disengage the needle housing 66 from the syringe-like body 12. A representative locking mechanism 86 is illustrated. In this embodiment, the reciprocal guide 50A is preferably made of spring steel with the engagement arm proximate end 54 being urged towards the syringe-like body 12 when attached.

As can best be seen in FIG. 4, the mount 46A includes a tooth 88 which has a sloped surface 90 that slopes away from the syringe-like body distal end 16 (FIG. 3) and into the oversized hole 48A. When the force applied to the engagement arm 52A is removed, the engagement arm 52A slides along the sloped surface 90 and is urged away from the syringe-like body 12 until notch 92 is aligned with the tooth 88. At that time, the inherent spring bias of the arm 52A urges the notch 92 over the tooth 88 which locks the engagement arm 52A in position. By locking the engagement arm 52A in position, the needle housing 66 is also locked in position and cannot be removed from operable engagement with the syringe-like body 12 while opposing faces 94, 96 of the tooth 88 and the notch 92, respectively, are engaged. To remove the needle housing 66, a force is applied in the direction indicated by arrow D (FIG. 3), and then the force is applied in the direction indicated by arrow C. The force in the direction indicated by arrow D disengages faces 94, 96 and permits the reciprocal movement of the reciprocal guide 50A.

Figure 5:
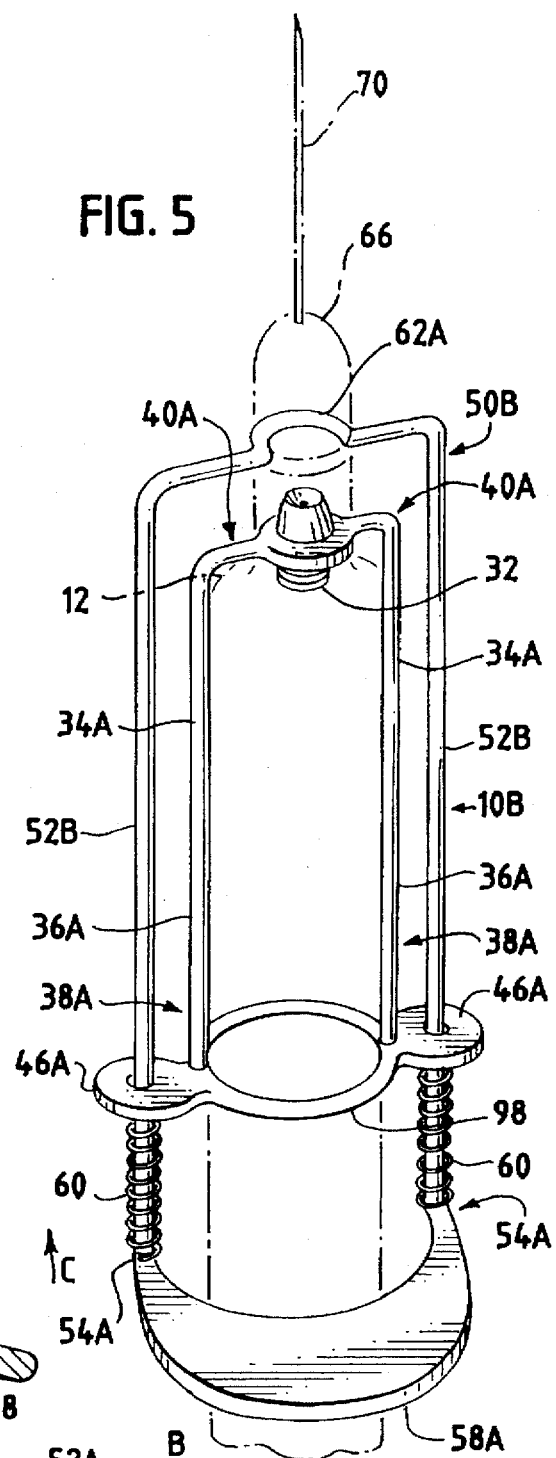
FIG. 5 is a perspective view of an alternative embodiment of the needle safety device showing the syringe-like body and needle housing in phantom.

FIG. 5 illustrates a further embodiment of the needle safety device 10B wherein the attachment to the syringe-like body 12 is still by the cooperation of protrusion 32 with a bore (not shown) of the syringe-like body 12. The guide support 34A has a pair of support arms 36A that meet adjacent the protrusion 32 at the support arm distal ends 40A and extend to a collar 98 at the support arm proximate ends 38A. The collar 98 extends about the syringe-like body 12. The reciprocal guide 50B includes a pair of engagement arms 52B that meet to form the needle housing holder 62A and extend adjacent and parallel to the syringe-like body 12 and the support arms 36A. Mounts 46A extending from the support arms 36A slidably receive the engagement arms 52B therethrough. The two engagement arms 52B are joined by a pad 58A at their proximate ends 54A. Springs 60 are disposed about the engagement arms 52B between the mounts 46A and the pad 58A. The operation of this embodiment is similar to that of the above-described embodiment.

In an embodiment that is not illustrated, a syringe-like body has the mount extending substantially perpendicular from it with the hole to receive the reciprocal guide. In this embodiment, there is no need for the guide support, and attachment to the syringe-like body is achieved by use of the mount.

The needle safety system can be retrofitted onto the syringe-like body using a threaded protrusion that threads into the bore. Alternatively, the protrusion can be pressure fitted into the bore. It is possible for the syringe-like body to have a protrusion that mates with a bore on the needle safety system. This embodiment is not illustrated.

Alternatively, the needle housing holder is a pair of spaced needle housing holders arranged and adapted to engage the needle housing on both sides of the radial ridge of a standard, conventional needle housing. This embodiment is not illustrated.

The needle safety device can be manufactured of any known material that is suitable for use in the medical industry and that can withstand the forces to which it is exposed. These materials include stainless steel and many plastics. The material should also be able to withstand sterilization, albeit this is not necessary if the needle safety system is disposable.

The use of a needle housing having a round cross section facilitates insertion of the needle housing holder into the groove because the orientation of the needle housing about its axis defined by the needle is irrelevant so long as the groove is aligned with the needle housing holder. The use of a needle housing having a round cross section also facilitates quick and easy removal of the needle housing from the holder because the needle housing has no sides or corners that can get hang up on the needle housing holder.

The retaining of the needle housing in a needle holder during guiding into and out of operable association of the needle with the syringe-like body permits control over the movement of the needle housing, and hence the needle, to permit the needle to be easily placed in the desired receptacle.

A person using the present needle safety device is protected from accidental puncture by the needle because, once the needle cap is removed, there is no need for the person to touch the needle or needle housing or recap the needle. This benefit is achieved by the use of a reciprocal guide that linearly guides the needle, held at its distal end, into and out of operable engagement with the syringe-like body when force is applied to the proximate end of the reciprocal guide.

This needle safety device is particularly well suited for use in the medical field to eliminate needle puncture wounds that can transmit deadly diseases.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

I claim:

1. A needle safety system for inhibiting accidental contact with a needle on a hollow syringe-like body for aspirating, injecting or collecting, the needle being associated with a needle body having a groove, the syringe-like body having a central axis and a distal end, the needle safety system comprising:

a needle safety device;

means for attaching the needle safety device to the syringe-like body wherein the attaching means comprises a protrusion and the syringe-like body to which the needle safety system attaches comprises a corresponding bore at the distal end of the syringe-like body, said protrusion being capable of operable association with the corresponding bore at the distal end of the syringe-like body;

a needle guide for assisting operable engagement of the needle with the syringe-like body, the needle guide being associated with the attaching means;

means for supporting the needle safety device to the syringe-like body, the supporting means extending from the attaching means, wherein the supporting means comprises a support arm extending from the attachment means and a mount on the support arm; and means for reciprocally guiding the needle linearly out of operable engagement with the syringe-like body, wherein the reciprocally guiding means comprises a spring biased engagement arm having proximate and distal ends, means for holding the needle at the distal end of the engagement arm and a pad at the proximate end of the engagement arm, the engagement arm being slidably received in the mount, the holding means being at least one C-shaped holding means that controls linear movement of the needle relative to the syringe-like body.

2. The needle recovery system of claim 1 further comprising a needle housing having the needle extending therethrough, the needle housing being capable of operable association with the holding means.

3. The needle recovery system of claim 2 wherein the needle housing defines a recess therein to receive the syringe-like body.

4. The needle recovery system of claim 2 wherein the needle housing defines a recess therein to receive the needle guide.

5. The needle recovery system of claim 1 further comprising a needle housing having a radial ridge wherein the holding means is a pair of C-shaped holding means adapted and arranged to engage the needle housing about the radial ridge.

6. A needle safety system for inhibiting accidental contact with a needle on a hollow syringe-like body for aspirating, injecting or collecting, the needle being associated with a needle body having a groove, the syringe-like body having a central axis and a distal end, the needle safety system comprising:

a needle safety device;

means for attaching the needle safety device to the syringe-like body wherein the attaching means comprises a bore capable of operable association with a corresponding protrusion at the distal end of the syringe-like body;

a needle guide for assisting operable engagement of the needle with the syringe-like body, the needle guide being associated with the attaching means;

means for supporting the needle safety device to the syringe-like body, the supporting means extending from the attaching means, wherein the supporting means comprises a support arm extending from the attachment means and a mount on the support arm; and means for reciprocally guiding the needle linearly out of operable engagement with the syringe-like body, wherein the reciprocally guiding means comprises a spring biased engagement arm having proximate and distal ends, means for holding the needle at the distal end of the engagement arm and a pad at the proximate end of the engagement arm, the engagement arm being slidably received in the mount, the holding means being at least one C-shaped holding means that controls linear movement of the needle relative to the syringe-like body.

7. A needle safety system, for inhibiting accidental contact with a needle on a hollow syringe-like body for aspirating, injecting or collecting, the syringe-like body having a central axis and a distal end, the needle safety system comprising:

a needle safety device;

means for attaching the needle safety device to the syringe-like body, said attaching means having a frusto-conical needle guide for assisting operable engagement of the needle with the syringe-like body, the needle guide being associated with the attaching means;

means for supporting the needle safety device to the syringe-like body, the supporting means extending from the attaching means; and means for reciprocally guiding the needle linearly out of operable engagement with the syringe-like body while maintaining control of the needle, the guiding means being in operable association with the supporting means.

8. A needle safety system, for inhibiting accidental contact with a needle on a hollow syringe-like body for aspirating, injecting or collecting, the syringe-like body having a central axis and a distal end, the needle safety system comprising:

a needle safety device;

means for attaching the needle safety device to the syringe-like body;

means for supporting the needle safety device to the syringe-like body, the supporting means extending from the attaching means; and means for reciprocally guiding the needle linearly out of operable engagement with the syringe-like body while maintaining control of the needle, said guiding means has a distal end and comprises means for holding the needle at the distal end, and the guiding means being in operable association with the supporting means, said holding means is a C-shaped holding means that controls linear movement of the needle along the central axis of the syringe-like body.

9. The needle safety system of claim 8 wherein the C-shaped holding means inhibits linear movement of the needle relative to the syringe-like body when the needle is in operative engagement with the syringe-like body.

10. A needle safety system, for inhibiting accidental contact with a needle on a hollow syringe-like body for aspirating, injecting or collecting, the syringe-like body having a central axis and a distal end, the needle safety system comprising:

a needle safety device;

means for attaching the needle safety device to the syringe-like body;

means for supporting the needle safety device to the syringe-like body, the supporting means extending from the attaching means; and means for reciprocally guiding the needle linearly out of operable engagement with the syringe-like body while maintaining control of the needle, the guiding means being in operable association with the supporting means, wherein the guiding means comprises a spring biased engagement arm.

11. The needle safety system of claim 10 wherein the guiding means has a proximate end and comprises a pad at the proximate end.

12. The needle safety system of claim 10 wherein the spring biased engagement arm has proximate and distal ends, means for holding the needle at the distal end of the engagement arm and a pad at the proximate end of the engagement arm.

13. The needle safety system of claim 10 wherein the supporting means comprises a support arm.

14. The needle safety system of claim 10 wherein the supporting means comprises a mount for slidably receiving the guiding means.

15. The needle safety system of claim 10 wherein the supporting means comprises a support arm extending from the attachment means and a mount for slidably receiving the guiding means, the mount being on the support arm.

16. The needle safety system of claim 10 wherein the attaching means comprises a protrusion and the syringe-like body to which the needle safety system attaches comprises a corresponding bore at the distal end of the syringe-like body, said protrusion being capable of operable association with the corresponding bore at the distal end of the syringe-like body, the supporting means comprises a support arm extending from the attachment means and a mount on the support arm and the guiding means comprises the spring biased engagement arm having proximate and distal ends, means for holding the needle at the distal end of the engagement arm and a pad at the proximate end of the engagement arm, the engagement arm being slidably received in the mount.

17. The needle safety system of claim 10 further comprising a means for locking the needle safety system with the needle in operative engagement with the syringe-like body.

18. The needle safety system of claim 10 wherein the attaching means comprises a bore capable of operable association with a corresponding protrusion at the distal end of the syringe-like body, the supporting means comprises a support arm extending from the attachment means and a mount on the support arm and the guiding means comprises the spring biased engagement arm having proximate and distal ends, means for holding the needle at the distal end of the engagement arm and a pad at the proximate end of the engagement arm, the engagement arm being slidably received in the mount.

* * * * *